United States Patent [19]

Wimmer

[11] Patent Number: 5,399,731
[45] Date of Patent: Mar. 21, 1995

[54] PROCESS FOR THE PRODUCTION OF FATTY ACID ESTERS OF LOWER ALCOHOLS

[75] Inventor: Theodor Wimmer, Heiligenkreuz, Austria

[73] Assignee: Vogel & Noot Industrieanlagenbau Gesellschaft m.b.H., Graz, Austria

[21] Appl. No.: 834,255

[22] PCT Filed: Jun. 28, 1991

[86] PCT No.: PCT/AT91/00076
§ 371 Date: Mar. 10, 1992
§ 102(e) Date: Mar. 10, 1992

[87] PCT Pub. No.: WO92/00268
PCT Pub. Date: Jan. 9, 1992

[30] Foreign Application Priority Data

Jun. 29, 1990 [AT] Austria ................... 1386/90

[51] Int. Cl.$^6$ .............................................. C11C 3/10
[52] U.S. Cl. ........................ 554/167; 554/169; 554/227
[58] Field of Search ............... 554/167, 169, 227, 30

[56] References Cited

U.S. PATENT DOCUMENTS 2,360,844 10/1944 Bradshaw et al. ............... 260/410
4,303,590 12/1981 Tanaka et al. ..................... 554/164

FOREIGN PATENT DOCUMENTS 3020612 12/1980 Germany .
3107318 12/1981 Germany .
9105034 4/1991 WIPO .

OTHER PUBLICATIONS

Verlag Chemie, "Ullmanns Encyklopaedie der technischen Chemie" 4th Edition, vol. 11, p. 432, 1976.

*Primary Examiner*—José G. Dees
*Assistant Examiner*—D. D. Carr
*Attorney, Agent, or Firm*—Panitch Schwarze Jacobs & Nadel

[57] ABSTRACT

The invention relates to a process for the production of the fatty acid esters of lower monovalent alcohols by transesterification of fatty acid glycerides in the presence of basic catalysts. The process according to the invention is characterized in that the transesterification is carried out in the presence of 0.025 to 0.045 mols of an alkali or alkaline earth metal compound, preferably sodium hydroxide, potassium hydroxide, sodium or potassium alcoholate, based on 100 g of fatty acid glyceride and the subsequent purification of the fatty acid esters is effected by the addition of 0.3 to 3.0 percent of water by hydration and separation of the catalyst residues and other impurities. In contrast to the known processes, it is thus possible to obtain lower alcohols of any given high degree of transesterification and high purity from untreated oils and fats of natural origin with contents of up to 20 percent of fatty acids in the free state at ambient temperature and atmospheric pressure at minor alcohol excess by means of the simplest equipment.

16 Claims, No Drawings

PROCESS FOR THE PRODUCTION OF FATTY ACID ESTERS OF LOWER ALCOHOLS

FIELD OF THE INVENTION

The present invention relates to a process for the production of fatty acid esters and/or fatty acid ester mixtures of lower monovalent alcohols having 1 to 5 carbon atoms by transesterification of fatty acid glycerides with the lower alcohols in the presence of basic catalysts.

The fatty acid esters produced according to the invention are suitable depending on the starting materials used, for instance as pharmaceutical, dietetic or cosmetic raw materials, as diesel fuels, as fuel oils or as intermediate products for the production of further fatty acid derivatives such as fatty alcohols, tensides and the like as well as for the production of lubricants.

Due to their suitability as diesel fuels, fatty acid esters of this type have recently gained particular importance for reasons of environment protection, the replacement of fossil fuels by regenerable energy sources and the problems connected with agriculture.

BACKGROUND OF THE INVENTION

The production of such fatty acid esters has long been known. It is effected on an industrial scale mainly by the base-catalyzed transesterification of fatty acid glycerides with lower alcohols. The procedure basically being such that the fatty acid glycerides are brought into contact with the lower alcohol in the presence of a basic catalyst at reaction conditions differing as a function of the starting material. The reaction mixture, once the transesterification is completed, separating into a heavy phase of more or less pure glycerol and a light phase consisting of the fatty acid esters of the lower alcohols.

The reaction conditions depend on the respective type of fatty acid glycerides employed. It is known, for instance, that oils and fats of natural origin, such as they are normally used, depending on their origin and pretreatment, have a content in fatty acids in the free state of up to 20 percent and more, can be transesterified in the presence of basic catalysts at temperatures around 240° C. and a pressure of about 100 bar at a seven to eight-fold molar excess of alcohol. (Ullmann, Enzyklopadie d. techn. Chemie, 4th edition, vol. 11, page 432 (1976)).

It is further known that such transesterification can be carried out at temperatures around the boiling point of the alcohol used and at normal or only slightly increased pressure at slight excess of the lower alcohols if the oils and fats employed are first deacidified by methods such as distillation, alkali extraction, acid-catalyzed preesterification and the like to a maximum content in free fatty acids of 0.5 percent and are subsequently dried.

It is further known that oils and fats are transesterified at normal pressure and environmental temperature with stoichiometric amounts of the lower alcohols in the presence of 1.0 to 1.7 percent by weight of potassium hydroxide based on the weight of the fat or oil employed. A substantial share of the known processes is dedicated to the purification of the fatty acid esters, in particular the elimination of the catalyst used.

The substantial drawbacks of the known processes reside in the fact that in the case of the application of high temperatures and pressures as well as excesses of alcohol, expensive reactors are necessary and high energy costs are incurred. Otherwise, the oils and fats used will have to be deacidified and dried, which also calls for expensive equipment. Additionally, the degrees of transesterification are too low and/or the contents in residual glycerol are too high, which is particularly the case in processes employing low alcohol excesses or stoichiometric amounts of alcohol, which for most intended uses calls for a subsequent distillation of the fatty acid esters. The removal of the catalyst, if this is effected by washing with water, causes considerable difficulties in the subsequent phase separation due to the formation of emulsions, or, if the catalyst is removed by washing with acids, a considerable amount of fatty acids in the free state is transferred to the ester phase. Further, in case an ion exchanger is used, the drawbacks connected with the regeneration and the effluents accumulating thereby must be coped with.

A further disadvantage common to all the known processes is that they can only be carried out by means of expensive or elaborate equipment and the technical expenditure connected therewith. Thus, they are economically unfeasible in small and minimum scale systems.

As a result, there was a demand for a process which is free of the aforementioned drawbacks and permits the production of such fatty acid esters from fatty acid glycerides of any given origin in purified or unpurified form especially with high contents in fatty acids in the free state at ambient temperatures and atmospheric pressure and the lowest possible alcohol excesses at any given and nearly one hundred percent degrees of transesterification at a minimum of technical and equipment expenditure, which process was to be suitable for large industrial systems as well as small and minimum scale systems.

SUMMARY OF THE INVENTION

It was surprisingly found that the aforementioned disadvantages can be avoided and that the requirement mentioned above can be met by carrying out the transesterification of fatty acid glycerides with 1.10 to 1.80 mols of a lower alcohol based on 1 mol of fatty acid bound as glyceride in the presence of an alkali or alkaline earth metal compound in the form of an oxide, hydroxide, hydride, carbonate, acetate or alcoholate. Preferably, the transesterification is carried out in the presence of sodium hydroxide or potassium hydroxide. The sodium and potassium alcoholates of the lower monovalent alcohols have 1 to 5 carbon atoms in an amount of at least 0.025 mols, preferably 0.030 to 0.045 mols, based on 100 g of the fatty acid glyceride used plus the amounts of the alkali or alkaline earth metal equivalent to the free fatty acids contained in the fatty acid glycerides used. Subsequent to the completed transesterification and the separation of the glycerol phase, 0.1 to 5 percent based on the ester phase of water or a diluted organic or inorganic acid are added with stirring to remove residual impurities such as in particular glycerol or catalyst residues, the amount depending on the amount of alkali or alkaline earth metal remaining in the ester phase and preferably ranging between 0.3 and 3 percent, and withdrawing the heavy phase after it has settled. The transesterification can be carried out in one or several stages. The fatty acid glyceride is either transesterified with the total amount of lower alcohol and catalyst or a first stage is carried out with only a portion of the amount of lower alcohol and catalyst required for the transesterification. The remaining amount(s) of lower alcohol and catalyst required for the transesterification are added in the same manner, subsequently to completed settling and separation of a glycerol phase, in a second stage or in several further stages. The two- and multiple-stage operations entail the advantage of a further reduction of the alcohol excess.

If the transesterification is carried out in a two-stage operation, 6/10 to 9/10 of the total amount of lower alcohol and catalyst required are preferably added in the first stage, while 1/10 to 4/10 are added in the second stage. In two- or multiple-stage operation, water can be added immediately after the second or the respective last stage, i.e., without previous separation of the glycerol phase formed in the second or last stage.

DESCRIPTION OF THE PREFERRED EMBODIMENTS

Transesterification according to the process of the present invention is preferably carried out at ambient temperatures of about +5° C. to +40° C. and atmospheric pressure and can be carried out in any given open or closed container of any given dimensions preferably provided with a discharge orifice in the bottom. At batch volumes of about 2,000 liters, stirring can be done manually by means of an electrically or compressed air-operated simple impeller agitator or, with larger volumes, conveniently in closed containers with fixedly mounted agitators. The required manipulations can be carried out manually or automated if required.

If suitable metering apparatus, a suitable reactor and an appropriate monitoring system are provided, the process can be carried out continuously. Suitable fatty acid glycerides are triglycerides naturally occurring as vegetable oils and fats such as soybean oil, palm oil and palm fat, coconut oil and coconut fat, sunflower oil, rapeseed oil, cottonseed oil, linseed oil, castor oil, peanut oil, olive oil, safflower oil, evening primrose oil, borage oil, carobseed oil and the like as well as mono-, di- and triglycerides isolated or produced by means of interesterification or synthetically, such as trioleine, tripalmitine, tristearol, glycerol monooleate, glycerol monodistereate and the like isolated or recovered by means of interesterification or produced synthetically from the aforementioned vegetable oils and fats, but also waste oils such as, e.g., spent deep-frying oil.

The vegetable oils and fats can be used refined or unrefined and may contain up to 20 percent and more of fatty acids in the free state in addition to slimy substances, turbid substances and other impurities.

Suitable lower monovalent alcohols are those having 1 to 5 carbon atoms, for instance, methanol, ethanol, propanol, isopropanol, butanol, isobutanol, 3-methyl-1-butanol, fermentation (iso) amyl alcohol or neopentyl alcohol.

Suitable basic catalysts are alkali or alkaline earth metal compounds in the form of the oxides, hydroxides, hydrides, carbonates, acetates or alcoholates of the lower alcohols, but preferably sodium hydroxide, potassium hydroxide or sodium and potassium alcoholates of the lower monovalent alcohols with 1 to 5 carbon atoms.

Suitable organic or inorganic acids are e.g., acetic acid, oxalic acid, citric acid, succinic acid, organic sulfonic acids or sulfuric acid esters, hydrochloric acid, nitric acid, sulfuric acid or phosphoric acid diluted with water or diluted aqueous solutions of acid salts such as, e.g., potassium or sodium hydrogen sulfate or sodium or potassium dihydrogen phosphate.

There are two substantial characterizing features of the process according to the invention. Firstly, the amount of catalyst used, whereby any given high degrees of transesterification and a trouble-free sedimentation and separation of the glycerol phase can be achieved at ambient temperature and atmospheric pressure and low alcohol excess at high degree of contamination and high content in free fatty acids in the fatty acid glycerides used. Secondly, the addition of water or an organic or inorganic acid after transesterification, whereby a trouble-free elimination of the catalyst residues from the ester phase and other residual impurities such as glycerol, phosphatides and the like from the ester phase is made possible.

Known processes in which the removal of the catalyst residues from the ester phase is effected by one or several washing(s) with water or acids, result in great difficulties due to the formation of emulsions or of fatty acids in the free state and subsequent elaborate phase separation and drying. In contrast, the process according to the invention provides for the sedimentation of the heavy phase containing the added water and the aforementioned impurities and the catalyst residues without the formation of emulsions and the ester phase can be drawn off after several hours.

The addition of water characteristic for the present invention is not comparable to the conventional washing operations of the known processes, which is already evident from the small amounts of water preferably used according to the invention, i.e., of 0.3 to 3 percent based on the ester phase. Instead, what is involved in the present case is the hydration of the anhydrous catalyst and glycerol residues present in the fatty acid esters with the added water. In contrast to the washing operations according to the known processes, the fatty acid esters are virtually anhydrous after the addition of water according to the invention and the settling of the heavy phase. If required, the separation of the heavy phase can be accelerated by means of a coalescence separator. Instead of water, a diluted organic or inorganic acid such as acetic acid, oxalic acid, citric acid, succinic acid, organic sulfonic acid or organic sulfuric acid ester, hydrochloric acid, nitric acid, sulfuric acid, phosphoric acid or a diluted aqueous solution of an acid salt such as sodium or potassium hydrogen sulfate or sodium or potassium dihydrogen phosphate could be used, namely, in amounts of from 0.1 to 5 percent, preferably of from 0.3 to 3 percent. The concentration of the acid or the acid salt is selected so that it is at least equivalent, and exceeds by up to 100 percent, the amount of transesterification catalyst remaining in the ester phase. This embodiment is mainly used if very small amounts of residual catalyst are contained in the ester phase.

The glycerol phase accumulating in the process according to the invention may contain large amounts of soaps particularly when using fatty acid glycerides with high proportions of fatty acids in the free state. The glycerol phase as well as the heavy phase accumulating after the addition of water which also contains glycerol and soaps, can conveniently be processed with concentrated phosphoric acid, such as it is described in the "Process for the Treatment of the Glycerol Phase Accumulating in the Transesterification of Fats and Oils with Low Alcohols" (Austrian patent application A 2357/89) of the applicant.

The process according to the invention does not preclude that the fatty acid esters thus produced, should the intended use require it, be subjected to a further purification by conventional measures. For instance, measures such as vacuum distillation, elimination of residual amounts of lower alcohols by means of evaporation or blowing out, additional drying by means of silica gel, molecular sieves, coalescence aids or the like, removal of higher melting portions of fatty acid esters by freezing, color and odor improvement or reduction of the peroxide number by treatment with bleaching earths and the like or the addition of additives such as agents for lowering the solidification point, for improving viscosity, for inhibiting corrosion, for protection against oxidation, improving the cetane number and the like, may be used so as to adapt the produced fatty acid esters to the respective intended use in a known manner.

The advantages of the process according to the invention particularly reside in the following facts. The operation can be carried out at low excesses of lower alcohols at ambient temperatures of +5° to +40° C. and atmospheric pressure. The oils and fats used need not be subjected to any purification and can contain up to 20 percent and more of fatty acids in the free state in addition to slimy substances, phosphatides and other impurities. Any given high degree of transesterification, rendering any further purification, for instance, by means of distillation, redundant for most applications, can be obtained depending on the preferably cited amounts of lower alcohol and transesterification catalyst. For instance, if the fatty acid esters are to be used as diesel fuels, no washing operations with water or acids and no ion exchangers are required for removing the catalyst residues. The transesterification can be carried out, if necessary, at temperatures of +5° C. and less, which is particularly convenient with fatty acid glycerides with sensitive highly unsaturated fatty acids such as alpha and gamma linoleic acid, eicosapenta and docosahexaenoic acids and the like because it prevents isomerizations, which is significant for the use of such fatty acid esters for pharmaceutical, dietetic and cosmetic purposes. Also, the fatty acid esters can be produced in a technically extremely simple manner.

The invention is explained in detail by means of the following examples:

EXAMPLE 1

A solution of 1.83 g (0.033 mols) of potassium hydroxide in 19 ml of methanol is added to 100 g of deslimed and deacidified (acid number 0.07) rapeseed oil and stirred in a beaker of 250 ml cubical content by means of a magnetic agitator for 15 minutes. After being left to stand for one hour, the glycerol phase accumulated on the bottom of the beaker is drawn off, e.g., by sucking up in a pipette. 0.5 l of water are added and stirring is continued for 10 minutes. After having been left standing for 12 hours, the supernatant is decanted. It consists of virtually pure rapeseed fatty acid methyl ester without any detectable fatty acid mono-, di- or triglycerides and an ash content of 0.004 percent.

EXAMPLE 2

In a container with a cubical capacity of 2000 liters equipped with an agitator and a discharge device in the bottom, 1618 kg of unrefined rapeseed oil with a content of 2.25 percent of fatty acids in the free state are charged. A solution of 27.8 kg of industrial grade potassium hydroxide (corresponding to 24.5 kg of 100 percent KOH) in 240 l of methanol is added and stirring is continued for 20 minutes. After a sedimentation period of three and one-half hours, the glycerol phase on the bottom of the container is drained off and stirring is resumed after the addition of a solution of 6.9 kg of industrial grade potassium hydroxide (corresponding to 6.1 kg of 100 percent KOH) in 60 l of methanol and continued for 20 minutes again. After that, 80 kg of water are immediately added and stirring is continued for another five minutes. After being left standing overnight, the heavy phase is drained off from the bottom of the container. The supernatant is suitable for use as a diesel fuel without any further treatment. It contains less than 1.5 percent residual fatty acid glycerides and 0.008 percent ash.

EXAMPLE 3

5.2 g of potassium hydroxide are dissolved in 23 g of methanol and 20 g of this solution are added to 100 g of rapeseed oil with an acid number of 30 (about 15 percent of fatty acids in the free state) and stirred for 15 minutes by means of a magnetic stirrer. After one hour, the heavy phase containing glycerol and lime (calcium) soaps is drained off and the remaining amount of 8.2 g of the potassium hydroxide-methanol solution is added and stirring is again continued for 15 minutes. After one further hour, the heavier phase is drained off again, 3 ml of water are added and stirring is continued for further 10 minutes. After being left standing for two hours, the supernatant consisting of rapeseed fatty acid methyl ester is separated. It contains 1.6 percent residual fatty acid glyceride and 0.008 percent potassium.

EXAMPLE 4

2.0 g of potassium hydroxide are dissolved in 22 ml of methanol and added to 100 g of sunflower oil with an acid number of 5.2 and stirred for 20 minutes by means of a magnetic stirrer. After 48 hours, the settled glycerol phase is separated and the supernatant sunflower methyl ester is stirred for 10 minutes with 0.8 ml of a 10 percent aqueous orthophosphoric acid. After being left standing for 12 hours and separation of the heavy phase, a sunflower methyl ester with 0.5 percent residual fatty acid glycerides and 0.002 percent ash is obtained.

EXAMPLE 5

A solution of 2.5 g of potassium ethylate in 18.4 g of ethanol is added to 100 g of deacidified evening primrose oil (acid number 0.07) and stirred for 30 minutes by means of a magnetic stirrer at a temperature of 0° to 5° C. After two hours, the glycerol phase is separated and the supernatant is stirred for 5 minutes with 1 ml of water. After settling of the heavy phase, the supernatant ester is separated. It does not contain any detectable amounts of fatty acid glycerides and shows a potassium content of 15 ppm. The gas chromatograph of the fatty acids is identical with that of the evening primrose oil employed. No isomerizations occurred.

EXAMPLE 6

100 g of palm core oil with a saponification number of 250 and an acid number of 16 are stirred for 20 minutes with a solution of 2.5 g of sodium hydroxide in 22 ml of methanol. After being left standing for one hour, the glycerol phase is separated. 1.5 ml of water are added to the supernatant and stirring is continued for another 10 minutes. After sedimentation of the heavy phase, the supernatant palm core methyl ester contains 2 percent residual glyceride and 0.01 percent ash.

EXAMPLE 7

1.56 g of potassium metal are dissolved in 48 g of neopentyl alcohol and this solution is added to 100 g of refined coconut oil (saponification number 260, acid number 0.3) and stirred for 30 minutes by means of a magnetic stirrer. After being left standing for 24 hours, the glycerol phase is separated and the supernatant is stirred for 10 minutes with 3 ml of water. After sedimentation of the heavy phase, the supernatant coconut fatty acid neopentyl ester contains 1.3 percent residual fatty acid glycerides and 0.01 percent ash.

I claim:

1. A process for the production of fatty acid esters of lower monovalent alcohols with 1 to 5 carbon atoms by transesterification of fatty acid glycerides with the lower monovalent alcohols in the presence of basic catalysts and at a reaction temperature of between 5° C. and +40° C., wherein based on each 100 g of fatty acid glyceride, at least 0.025 mols of a basic alkali or alkaline earth metal compound, plus that amount of the alkali or alkaline earth metal compound which is equivalent to the fatty acids in the free state contained in the fatty acid glycerides employed, are used as transesterification catalyst at an excess of the lower monovalent alcohol of 1.10 mols to 1.80 mols per mol of fatty acid esterified with glycerol, and that after completion of the transesterification, 0.1 to 5.0 percent of a diluted organic or inorganic acid or a diluted aqueous solution of an acid salt, based on the weight of the fatty acid ester, are added with stirring and fatty acid ester is separated as supernatant after settling of a heavy phase.

2. The process according to claim 1, wherein the transesterification is carried out in multiple stages, and wherein 6/10 to 9/10 of the total amount of the lower alcohol and transesterification catalyst are employed in a first stage of the multiple-stage process, while 4/10 to 1/10 of the total amount of the lower alcohol and transesterification catalyst are used in a second stage of the multiple-stage process.

3. The process according claim 1, wherein the settling of a heavy phase following the addition of the diluted organic or inorganic acid or the diluted aqueous solution of an acid salt is accelerated by means of a coalescence separator.

4. The process according to claim 1, wherein the fatty acid glycerides are natural oils and fats, which may be refined or unrefined and contain up to 20 percent of fatty acids in the free state, and fatty acid glycerides isolated from said natural oils and fats or obtained therefrom by interesterification or synthetically.

5. The process according to claim 1, wherein the alkali or alkaline earth metal compounds are employed in the form of the oxides, hydroxides, hydrides, carbonates, acetates or alcoholates, of the lower monovalent alcohols.

6. The process according to claim 1, wherein methanol, ethanol, propanol, isopropanol, butanol, isobutanol, 3-methyl-1-butanol, amyl alcohols or neopentyl alcohol are used as the lower monovalent alcohols.

7. The process according to claim 1, wherein the transesterification catalyst is used in an amount of 0.030 to 0.045 mols per 100 g of fatty acid glyceride used plus that amount equivalent to the fatty acids in the free state contained in the fatty acid glycerides employed.

8. The process according to claim 1, wherein acetic acid, oxalic acid, citric acid, succinic acid, organic sulfonic acids, organic sulfuric acid semi-esters, hydrochloric acid, nitric acid, sulfuric acid, phosphoric acid, sodium hydrogen sulfate, potassium hydrogen sulfate, sodium or potassium dihydrogen phosphate are used as the diluted organic or inorganic acid or the diluted aqueous solution of an acid salt and the amount of the aforementioned acids and salts is selected in such a manner that it is at least equivalent to the amount of basic catalyst contained in the fatty acid ester phase.

9. The process according to claim 2, wherein the settling of a heavy phase following the addition of the diluted organic or inorganic acid or the diluted aqueous solution of an acid salt is accelerated by means of a coalescence separator.

10. The process according to claim 2, wherein the fatty acid glycerides employed are natural oils and fats such as soybean oil, palm oil, palmcore oil, coconut oil, sunflower oil, rapeseed oil, cottonseed oil, linseed oil, castor oil, peanut oil, olive oil, safflower oil, evening primrose oil, borage oil and carobseed oil which may be refined or unrefined and contain up to 20 percent of fatty acids in the free state and fatty acid glycerides such as trioleine, tristearol, tripalmitine or glycerol monoleate isolated from such fats and oils or obtained from them by interesterification or synthetically are employed.

11. The process according to claim 2, wherein the alkali or alkaline earth metal compounds are employed in the form of the oxides, hydroxides, hydrides, carbonates, acetates or alcoholates of the lower monovalent alcohols.

12. The process according to claim 2, wherein methanol, ethanol, propanol, isopropanol, butanol, isobutanol, 3-methyl-1-butanol, amyl alcohols or neopentyl alcohol are used as the lower monovalent alcohols.

13. The process according to claim 2, wherein the transesterification catalyst is used in an amount of 0.030 to 0.045 mols per 100 g of fatty acid glyceride used plus that amount equivalent to the fatty acids in the free state contained in the fatty acid glycerides employed.

14. The process according to claim 2, wherein acetic acid, oxalic acid, citric acid, succinic acid, organic sulfonic acids, organic sulfuric acid semi-esters, hydrochloric acid, nitric acid, sulfuric acid, phosphoric acid, sodium hydrogen sulfate, potassium hydrogen sulfate, sodium or potassium dihydrogen phosphate are used as the diluted organic or inorganic acid or the diluted aqueous solution of an acid salt and the amount of the aforementioned acids and salts is selected in such a manner that it is at least equivalent to the amount of basic catalyst contained in the fatty acid ester phase.

15. The process according to claim 4, wherein said natural oils and fats are selected from the group consisting of soybean oil, palm oil, palmcore oil, coconut oil, sunflower oil, rapeseed oil, cotton seed oil, linseed oil, castor oil, peanut oil, olive oil, safflower oil, evening primrose oil, borage oil and carobseed oil and said fatty acid glycerides are selected from the group consisting of trioleine, tristearol, tripalmitin, and glycerol monoleate.

16. The process according to claim 5, wherein said hydroxide is selected from the group consisting of sodium hydroxide and potassium hydroxide, and said alcoholate of lower monovalent alcohols is selected from the group consisting of sodium alcoholates of lower monovalent alcohol and potassium alcoholates of lower monovalent alcohol.

* * * * *